United States Patent
Morero et al.

(10) Patent No.: US 9,168,362 B2
(45) Date of Patent: Oct. 27, 2015

(54) DRUG ELUTING BALLOON FOR THE TREATMENT OF STENOSIS AND METHOD OF MANUFACTURING THE BALLOON

(75) Inventors: Massimo Morero, Roncadelle (IT); Giovanni Scalvini, Roncadelle (IT)

(73) Assignee: Invatec Technology Center Gmbh, Fravenfeld (CH)

( * ) Notice: Subject to any disclaimer, the term of this patent is extended or adjusted under 35 U.S.C. 154(b) by 165 days.

(21) Appl. No.: 13/885,377

(22) PCT Filed: Dec. 21, 2010

(86) PCT No.: PCT/EP2010/070423
§ 371 (c)(1), (2), (4) Date: Jun. 24, 2013

(87) PCT Pub. No.: WO2012/084024
PCT Pub. Date: Jun. 28, 2012

(65) Prior Publication Data
US 2013/0303982 A1  Nov. 14, 2013

(51) Int. Cl.
*A61M 31/00* (2006.01)
*A61M 37/00* (2006.01)
*A61M 25/10* (2013.01)
*A61L 29/16* (2006.01)

(52) U.S. Cl.
CPC .............. *A61M 25/104* (2013.01); *A61L 29/16* (2013.01); *A61M 25/1038* (2013.01); *A61L 2300/416* (2013.01); *A61L 2300/62* (2013.01); *A61L 2300/63* (2013.01); *A61M 25/1011* (2013.01); *A61M 2025/1004* (2013.01); *A61M 2025/105* (2013.01); *A61M 2025/1031* (2013.01); *A61M 2025/1052* (2013.01)

(58) Field of Classification Search
CPC .................. A61M 25/104; A61M 2025/1004; A61M 2025/1031; A61M 2025/105; A61M 2025/1052; A61M 25/1038; A61M 29/02; A61M 2025/1013; A61M 2025/1015; A61M 25/1011
See application file for complete search history.

(56) References Cited

U.S. PATENT DOCUMENTS

| 2004/0215227 | A1* | 10/2004 | McMorrow et al. ........... 606/191 |
| 2009/0054837 | A1* | 2/2009 | Von Holst et al. ....... 604/103.08 |
| 2010/0023106 | A1* | 1/2010 | Meyer et al. .................. 623/1.11 |

* cited by examiner

*Primary Examiner* — Rebecca E Eisenberg

(57) ABSTRACT

A drug eluting angioplasty balloon (1, 101) suitable to adopt a deployed configuration and a collapsed configuration, the balloon having an outer wall (10) disposed around a core (11) defining an axis (X). The balloon (1, 101) comprising in the collapsed configuration a plurality of folds (12, 12', 112) that are laid in a tangential direction about the core (11) and form a plurality of cavities (13a, 13b, 113) loaded with a drug (14), the cavities (13a, 13b, 113) are comprised between the folds (12, 12', 112), wherein the folds (12, 12', 112) originates from distinct longitudinal lines (25, 25', 125, 125') along the outer wall (10), are arranged in pairs and are circumferentially wrapped about the core (11) in such a way that a fold of one pair overlaps an adjacent fold of another pair and are wrapped in opposite directions.

19 Claims, 11 Drawing Sheets

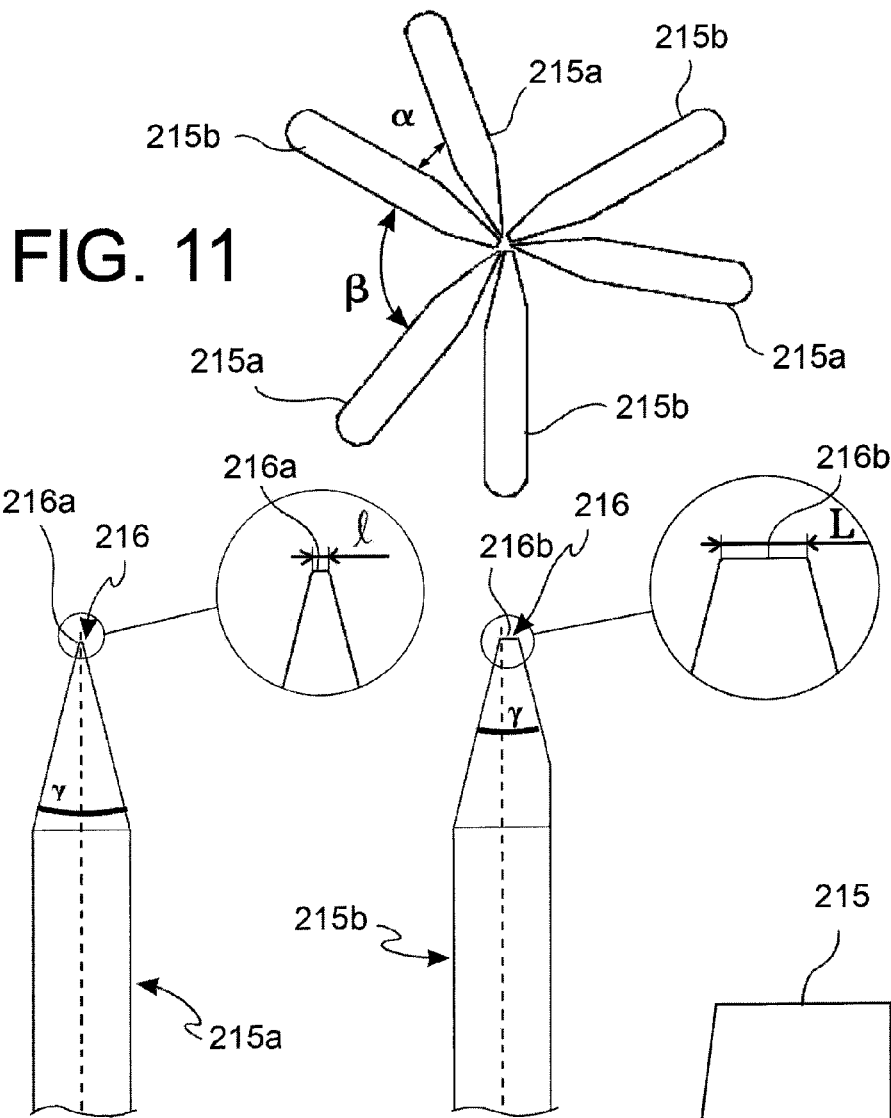
FIG. 11
FIG. 12A        FIG. 12B
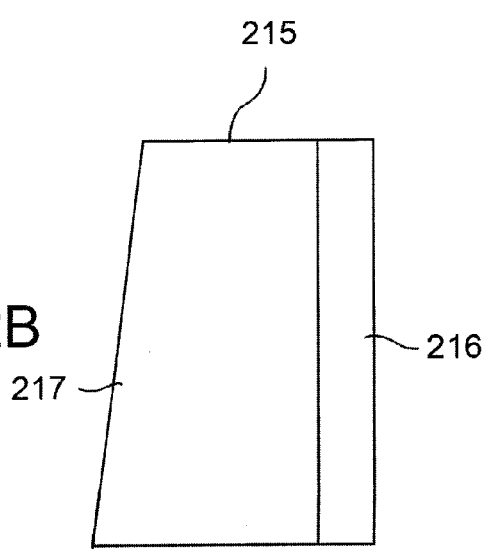
FIG. 13

DRUG ELUTING BALLOON FOR THE TREATMENT OF STENOSIS AND METHOD OF MANUFACTURING THE BALLOON

FIELD OF THE INVENTION

The present invention relates to a balloon catheter for angioplasty and pharmacologic treatment of stenosis. The invention further relates to a method for manufacturing the said balloon catheter.

BACKGROUND ART

Balloon catheters for the angioplasty treatment of stenosis within the human body circulatory system have been known for a long time. These catheters comprise a balloon at the distal end thereof. The balloon catheter is inserted within the blood vessels with the balloon in a deflated configuration and is brought proximate to the site of stenosis. At this point, the balloon is inflated for a relatively short time span to obtain the dilation of the vessel and concomitantly a mechanical treatment of the stenosis, which is suitable to restore the section of the blood vessel. However, this mechanical action may cause in some patients, at the site of intervention, a cell hyperproliferation known as restenosis, which may again lead to an obstruction of the blood vessel and to severe consequences to the patient.

It has been recently noted that the outcome of a conventional mechanical angioplasty intervention results to be dramatically improved when a drug suitable to prevent restenosis is used in association therewith. Suitable drugs for this kind of treatment are antiproliferative drugs. These drugs can be, for example: rapamycin, epothilone and mainly paclitaxel.

Attempts have already been made to coat the angioplasty balloon with a gelatinous layer consisting of a mixture of a suitable solvent and paclitaxel. Patent applications WO 2004/028610, WO 2004/028582, and WO 2002/076509 to Ulrich Speck describe the positioning of a lipophilic drug, such as paclitaxel, on the outer portion of an angioplasty balloon.

This known method, however, is not without defects.

In fact, in order to reach the site of stenosis, the balloon catheter is required to travel along a relatively long pathway within the healthy blood vessels, while being exposed to the blood stream. Along this pathway, the drug, even if lipophilic, is very likely to be partially removed from the balloon due to friction against the vessel walls or to the flushing and rinsing effect of the blood flow.

This at least partial removal of drug from the balloon determines some undesirable consequences. Firstly, the administration of the drug to the stenosis area is lower than expected and a priori unknown. Secondly, an amount of the drug is dispersed in unintended districts of the body, with consequent undesirable secondary effects due to the intrinsic toxicity of the antiproliferative drug that is used.

Moreover, it has been observed that after the drug has been carried close to the stenosis, it can immediately be lost after the normal blood flow has been restored.

An angioplasty balloon catheter that comprises a chamber between the folds filled with a drug is known. It has been observed however that, when immersed into a blood environment, this type of balloon may partially lose an amount of drug before reaching the final destination, as the folds tend to open or the plasma tends to reach the cavity under the folds by capillarity.

SUMMARY OF THE INVENTION

An object of the present invention is to provide an angioplasty balloon catheter and a method for manufacturing the same, which obviates at least partially the drawbacks mentioned above with reference to the prior art.

Another object of the present invention is to provide an angioplasty balloon catheter which allows administering a substantial amount of the drug provided thereon to the stenosis area when it is introduced within the patient's body.

A further object of the present invention is to provide a drug eluting angioplasty balloon catheter, which restrains the dispersion of the drug in unintended districts of the patient's body.

A further object of the present invention is to provide a drug eluting angioplasty balloon catheter which allows to deliver substantially all the drug loaded thereon to the site of intervention.

Another object of the present invention is to provide an angioplasty device which restrains the dispersion of the drug after it has been released, thereby preventing the rinsing effect that commonly occurs when the normal blood flow has been restored.

Another object of the present invention is to provide a folded angioplasty balloon which effectively keeps the drug under the folds when exposed to a blood stream.

A further object of the invention is to provide a folded angioplasty balloon wherein a drug reservoir is created under the folds and wherein the surface of the balloon outside the folds is free of drug.

A further object of the invention is a method of folding a balloon catheter and an apparatus to perform such a method.

A further object of the invention is a method of coating the surface of an angioplasty balloon with a drug to obtain a folded drug eluting angioplasty balloon, wherein a substantial amount of the drug is included under the folds.

Another object of the invention is a method of coating the surface of an angioplasty balloon with a drug to obtain a folded drug eluting angioplasty balloon, wherein the balloon surface outside the folds is substantially free of drug.

Another object of the present invention is a method of coating the surface of a folded angioplasty balloon with a drug, wherein a substantial amount of the drug is included under the folds.

The present invention provides an angioplasty balloon suitable to adopt a deployed configuration and a collapsed configuration, having an outer wall disposed around a core defining an axis, the balloon comprising in the collapsed configuration a plurality of folds that are laid in a tangential (or circumferential winding) direction about the balloon and thus form a plurality of cavities for loading with a drug, wherein the said folds originate from distinct longitudinal lines along the outer wall of the balloon and are arranged in pairs, and wherein the said folds are wrapped in such a way that a fold of one pair overlaps an adjacent fold of another pair.

The present invention provides for a method for obtaining a folded angioplasty balloon, which comprises:
  forming a plurality of folds wherein the said folds originates from distinct longitudinal lines and are arranged in pairs;
  wrapping the said folds in such a way that a fold of one pair overlaps an adjacent fold of another pair to create cavities suitable for receiving a drug.

According to an embodiment, the method comprises the step of filling the cavities with said drug.

According to a further embodiment, the method comprises the step of applying a plurality of bands of drug. Preferably, the step of applying the drug is carried out before the step of forming a plurality of folds.

Furthermore, the present invention provides for an apparatus for creating folds on an angioplasty balloon, the said apparatus having a longitudinal axis and being apt for the said angioplasty balloon to be inserted along the said longitudinal axis, the apparatus comprising a plurality of radially movable blades that are positioned with their blade edge facing toward the said longitudinal axis, the said blades being movable in a radial plane which contains the longitudinal axis of the apparatus, or in a plane parallel thereto, from a retracted position to an advanced position, wherein the blades are arranged in pairs with a predefined geometry, which is in relation with the geometry of the folds of the angioplasty balloon, wherein an angle α is defined between two blades of a pair and an angle β is defined between a blade of a pair and an adjacent blade of another pair of blades, wherein β is greater than α.

Moreover, the present invention provides for a method for obtaining a folded angioplasty balloon, which comprises:
  a) inserting the said angioplasty balloon along the longitudinal axis of the apparatus as defined above;
  b) wholly or partially inflating the said angioplasty balloon, wherein steps a) and b) are performed in any order;
  c) moving the blades from a retracted position to an advanced position wherein the edge tip of the blades presses the surface of the angioplasty balloon;
  d) deflating the angioplasty balloon in order to obtain a collapsed folded balloon wherein a plurality of folds and first and second gaps between the folds are created;
  e) wrapping a fold of one pair in one direction and then an adjacent fold of another pair in the opposite direction, so that the said second gaps result to be covered by the wrapped folds and the folds substantially overlap;
  f) repeating step e) for each pair of folds, so that a wrapped folded angioplasty balloon is obtained, wherein cavities are created under the folds, the said cavities being apt to be loaded with a drug.

According to an embodiment, in step c) the blades are moved synchronously from the said retracted position to the said advanced position to synchronously press the surface of the angioplasty balloon.

According to an embodiment, in step e) the fold of one pair is wrapped in one direction and the other fold of the same pair is wrapped in the same direction, so that the said second gaps result to be covered by the wrapped folds and the folds substantially overlap.

As used in the present description, the terms "site of stenosis" and "site of intervention" are synonymous and refer to the section or sections of a blood vessel which are affected by stenosis and which require an angioplasty intervention.

As used in the present description, the term "stenosis area" refers to the surface of a blood vessel which is affected by stenosis.

As used in the present description, the term "drug" or "antiproliferative drug" means a drug which is able to treat or prevent restenosis, particularly via an antiproliferative effect.

As used in the present description, the term "drug eluting angioplasty balloon" refers to an angioplasty balloon whose external surface or parts thereof is loaded with an amount of drug or it is coated by a drug.

As used in the present description, the term "substantial amount of drug" means an amount which is greater than 70% or greater than 80% or even greater than 90%, with respect to the amount of drug loaded onto the balloon.

As used in the present description, the term "folded angioplasty balloon" refers to an angioplasty balloon which, in its collapsed state, is folded to form overlapping or partially overlapping wrapped folds, also sometimes referred to as "wings."

Further embodiments, features and advantages of the present invention will be better understood from the following detailed description, which is given below by way of non-limiting illustrations.

BRIEF DESCRIPTION OF THE DRAWINGS

FIG. 11 is a schematic top view of the blade arrangement in the apparatus of FIG. 10;
FIGS. 12A and 12B are schematic top views of a particular of the blades of FIG. 11;
FIG. 13 is a side view of a blade of FIG. 11.

DETAILED DESCRIPTION OF THE INVENTION

Figure 1:
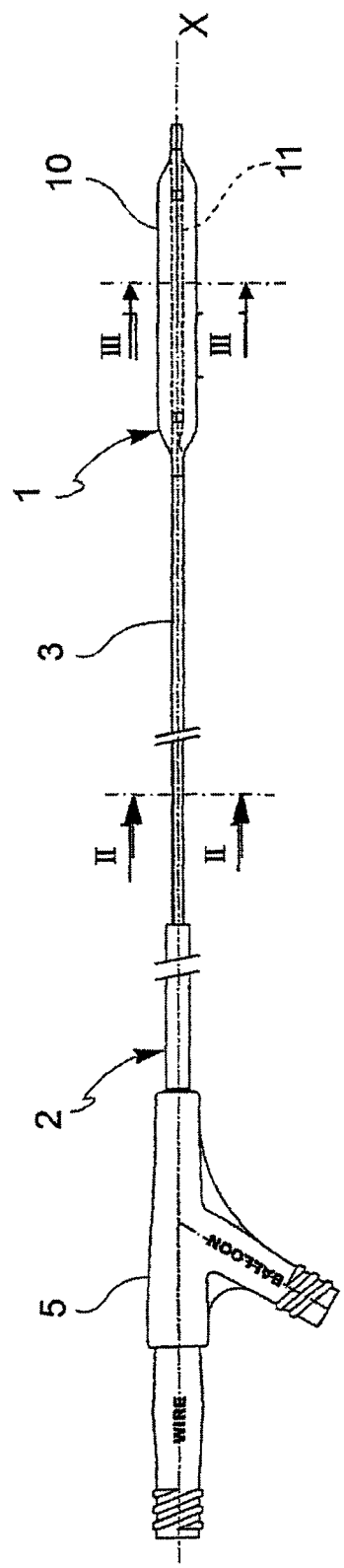
FIG. 1 is a side view of an angioplasty balloon catheter.
Figure 2:
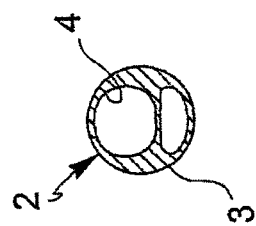
FIG. 2 is a sectional view along the lines II-II in FIG. 1.
Figure 3:
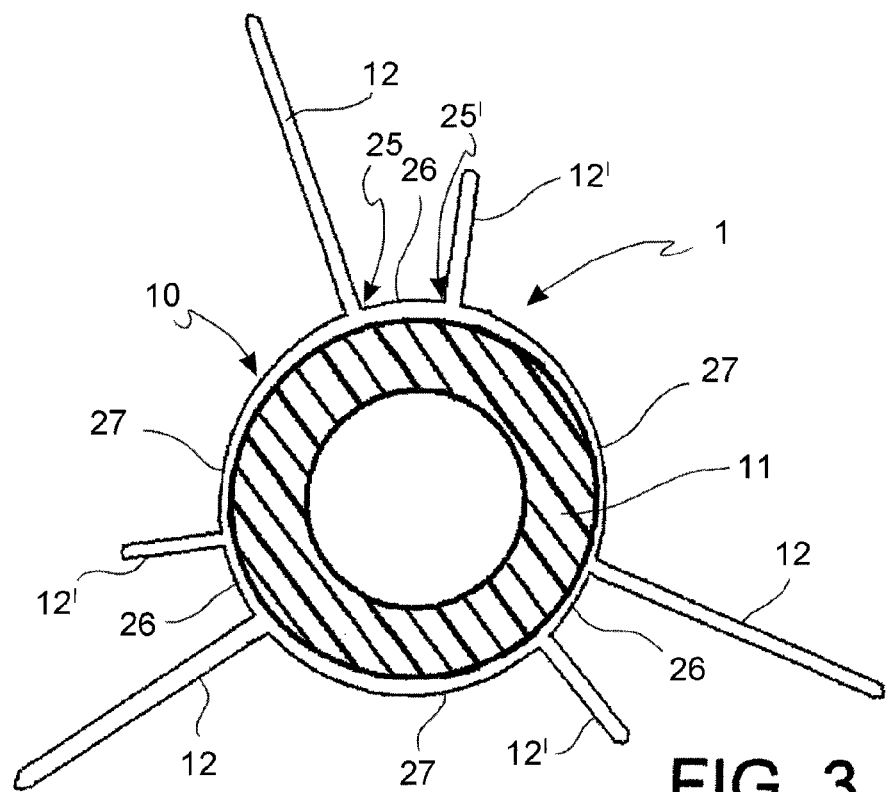
FIG. 3 is a sectional view along the lines III-III of the folded balloon catheter of FIG. 1 according to a first embodiment of the invention, in an unwrapped collapsed configuration.

With reference to the figures, an angioplasty balloon, indicated with the numeral 1, is mounted at the distal end of a catheter 2.

The catheter 2 further comprises an elongated tubular body 3 that is provided with a plurality of lumens 4, 4' (passages for the guide-wire and for inflating or deflating the balloon, respectively), and a connector means 5 at the proximal end thereof. In the figure, the lumens 4, 4' are positioned side by side, but a coaxial arrangement may also be foreseen.

The balloon 1 is suitable to alternatively adopt a deployed configuration and a collapsed configuration. The balloon is brought to the deployed configuration by means of the injection of a pressurized inflating fluid, and vice versa it is brought to the collapsed configuration by means of the suction of the same inflating fluid.

The angioplasty balloon of the invention can be manufactured in any polymeric material that is conventionally used for these applications, such as, without limitation, polyamide materials, their blends or copolymers thereof.

In the collapsed configuration, the balloon is suitable to be inserted within the circulatory system of a patient's body and to be advanced along a vessel to reach a vessel section that is affected by stenosis. The balloon 1 is further suitable to apply, when it passes from the collapsed configuration to the deployed configuration, a radial force to the stenosis area such as to expand the latter and restore the nominal section of the vessel.

The balloon 1 comprises an outer wall 10 disposed around a core 11. The core 11 represents a distal region of the catheter 2, and in particular it is a single lumen extension of the tubular body 3. The core 11 defines an axis X about which the balloon 1 is developed and comprises a lumen for receiving a guidewire.

By the term "axial" it is meant the direction of a straight line parallel to the axis X. By the term "radial" it is meant the direction of a half-line originating on the axis X and perpendicular thereto. Finally, by the term "circumferential" (or "tangential") it is meant the direction of a circumference (or a tangent thereto) that is centered on the axis X and lying on a plane perpendicular to the axis X.

In the collapsed configuration, the balloon 1 according to the invention, as shown in FIGS. 3 to 7 and 18, comprises a plurality of folds 12, 12' or 112 that are formed about the core 11.

According to the present invention, the folds 12, 12', 112 are arranged in pairs.

According to an embodiment of the invention, a fold 12, 112 of a pair and the adjacent fold 12', 112 of an adjacent pair are circumferentially wrapped in opposite directions, i.e. if a fold is wrapped clockwise, the adjacent fold is wrapped counter-clockwise, or vice versa, so that the two adjacent folds overlap.

The folds 12, 12', 112 according to the invention are single-folded, which means that they are folded only once.

When two adjacent folds 12, 12', 112 in different pairs are wrapped to overlap, one or more cavities 13a, 13b, 113, 213a and 213b are created. Such cavities extend longitudinally along the balloon length.

Figure 9:
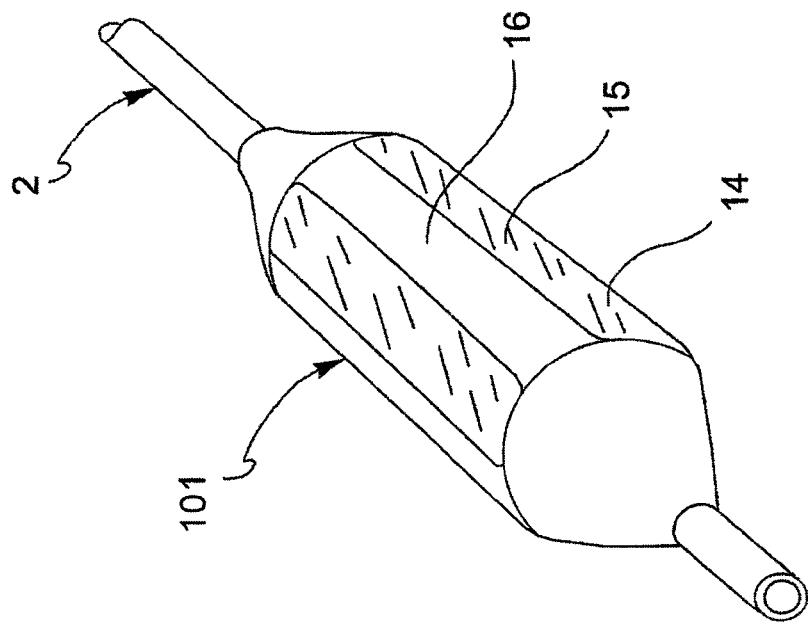
FIG. 9 is a perspective view of an angioplasty balloon according to an embodiment of the invention, in a deployed configuration.

A drug 14 is loaded onto the balloon (represented for instance in FIG. 9).

Figure 8:
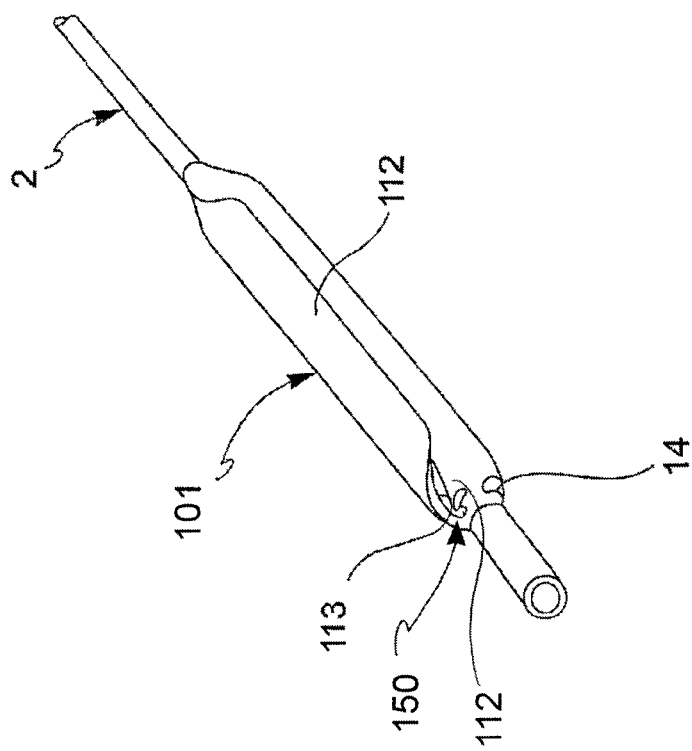
FIG. 8 is a perspective view of the angioplasty balloon of FIG. 7.

In particular, a drug 14 is positioned inside the cavities 13a, 13b, 113, 213a and 213b (represented for instance in FIG. 8).

As shown in FIGS. 4, 5, 7 and 18, the folds 12, 12', 112 are wrapped in such a way that a fold of one pair overlaps an adjacent fold of another adjacent pair.

In a preferred embodiment, the folds 12, 12', 112 are wrapped in such a way that a fold of one pair substantially overlaps an adjacent fold of another pair.

The term "substantially overlaps" as used herein means that the fold of one pair overlaps for at least 60% of its circumferential length the adjacent fold of another pair.

Preferably, the term "substantially overlaps" means that the fold of one pair overlaps for at least 70% of its circumferential length the adjacent fold of another pair.

More preferably, the term "substantially overlaps" means that the fold of one pair overlaps for at least 80% of its circumferential length the adjacent fold of another pair.

According to a different embodiment, the folds 12, 12', 112 are wrapped in such a way that a fold of one pair completely overlaps an adjacent fold of another pair.

The term "completely overlaps" as used herein means that the fold of one pair overlaps for its whole circumferential length the adjacent fold of another pair in such a way that said adjacent fold is completely covered.

As shown in FIGS. 4, 5, 7 and 18, the folds 12, 12', 112 are wrapped in such a way that a fold of one pair overlaps and adheres to an adjacent fold of another pair. This means that a fold of one pair not only overlaps the adjacent fold of an adjacent pair, but also that the two folds contact and touch each other along their circumferential extension which is subjected to overlapping.

In particular, the fold of one pair overlaps and adheres for at least 60% of its circumferential length to the adjacent fold of another pair.

Preferably, the fold of one pair overlaps and adheres for at least 70% of its circumferential length to the adjacent fold of another pair.

More preferably, the fold of one pair overlaps and adheres for at least 80% of its circumferential length to the adjacent fold of another pair.

According to another embodiment, the fold of one pair overlaps and adheres for the whole circumferential length the adjacent fold of another pair in such a way that said adjacent fold is completely covered and sealed by the overlapping fold.

The combination of overlapping and adhesion (contact) between the folds is important since it assures a maximized tightness of the cavities 13a, 13b, 113, 213a and 213b. In fact, the cohesion forces between the polymeric surfaces of the contacting folds are believed to help in creating very protective cavities for a safe and lasting storage of the drug 14 until the balloon reaches the intervention site. The larger the contact surface between two overlapped folds, the stronger are the cohesion forces that tend to keep the folds adhered one to each other. Therefore, the unwrapping of the folds is advantageously prevented.

In the embodiment shown in FIG. 9, the balloon 1 according to the invention, while in the deployed configuration, comprises a plurality of bands 15 of drug 14 that are axially arranged along the balloon outer wall 10. The bands 15 of drug 14 are alternated in the circumferential direction with strips 16 in which the drug 14 is not provided and thus the outer wall 10 is directly exposed.

The number of bands 15, and consequently the number of strips 16, depends on the number of folds 12, 12' or 112. For example, the presence of three pairs of folds such as three folds 12 and three folds 12' or of six folds 112, when the balloon is in the collapsed configuration, determines the presence of three bands 15 of drug 14 that are alternated with three strips 16 free of drug.

According to an embodiment of the invention, as shown in FIGS. 3, 4, 5 and 18, three folds 12 of a first length and three folds 12' of a second length are provided when the balloon is in a collapsed configuration, wherein the said first length is greater than the said second length, so that the balloon, when in the collapsed configuration, does not have a plane of symmetry containing the axis X of the balloon. This particular configuration of the collapsed balloon will be indicated below as the "asymmetrical configuration" of the angioplasty balloon.

The longer folds 12 and the shorter folds 12' originate from distinct axial lines 25, 25' on the surface of the balloon 1 and form a pair of folds 12, 12'. In the figures, references 25 and 25' indicate distinct points since these figures represent cross sections of the balloon.

Each of the longer and shorter folds 12, 12' of a pair is separated by a first gap 26 extending circumferentially between axial lines 25, 25' when the balloon is in a collapsed configuration.

A second gap 27, having a greater extension than the first gap 26, circumferentially separates a longer fold 12 of a pair from a shorter fold 12' of an adjacent pair.

The extension of the first gap 26 may tend towards zero in order to maximize the second gap 27 for the reason that will become clear below.

Figure 4:
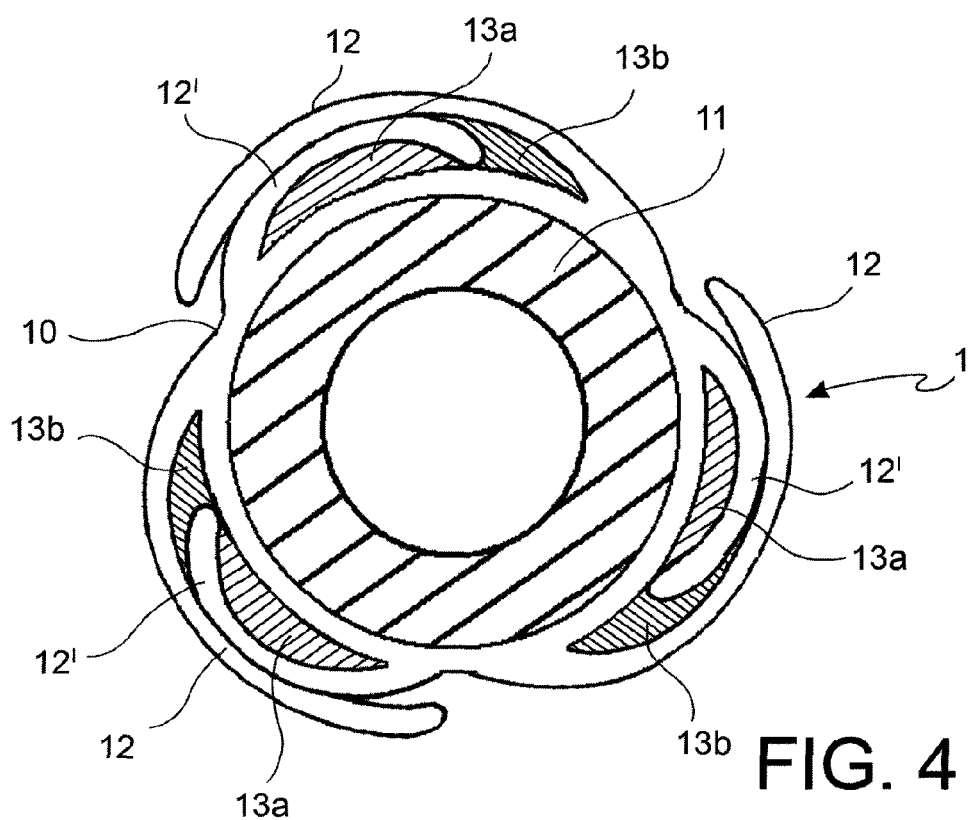
FIG. 4 is a sectional view of the folded balloon catheter of FIG. 3, in a wrapped collapsed configuration.
Figure 5:
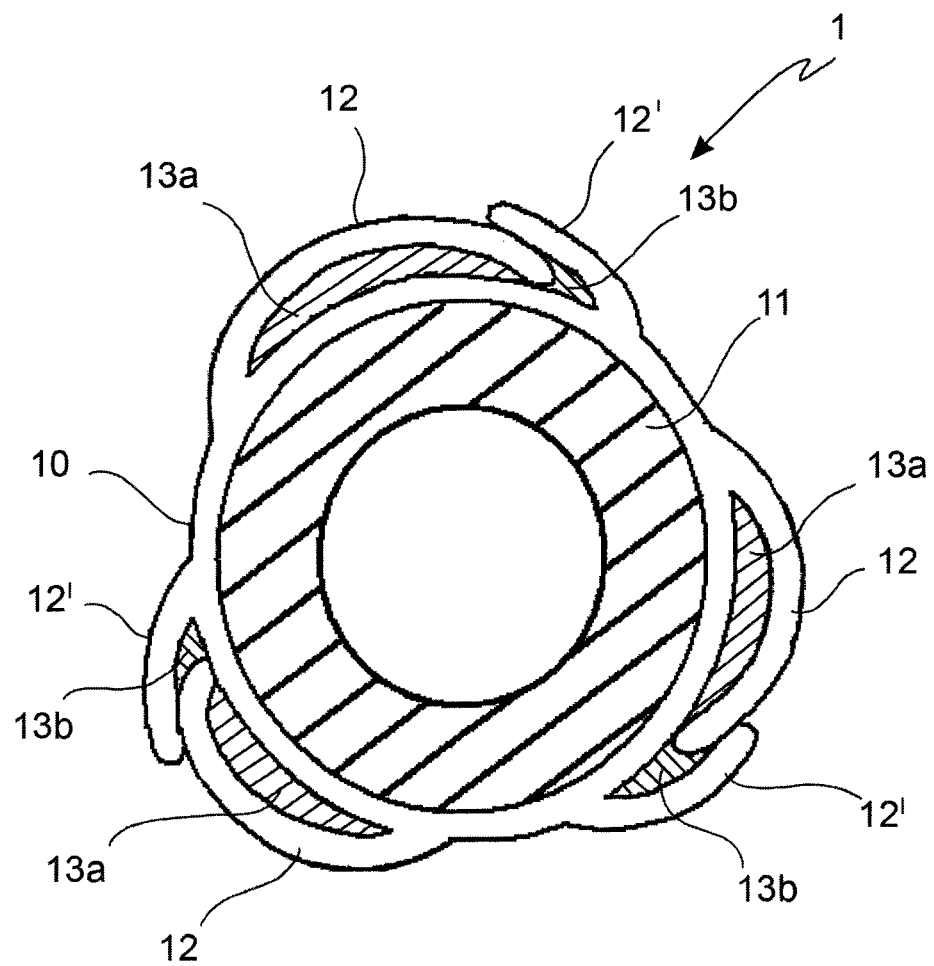
FIG. 5 is a sectional view of the folded balloon catheter of FIG. 3, in a different wrapped configuration.

According to an embodiment of the present invention, as shown in FIGS. 4 and 5 the folds 12, 12' are circumferentially wrapped in such a way that a shorter fold 12' of one pair is wrapped in one direction—for example, in a clockwise direction—and an adjacent longer fold 12 of an adjacent pair is wrapped in the opposite direction—for example, in a counter-clockwise direction—so that the second gap 27 is covered by the wrapped folds 12, 12'.

Wrapping the folds as described above may be performed in accordance with the following embodiments. The first possibility (shown in FIG. 4) is that the shorter fold 12' is wrapped before the longer fold 12, so that this latter overlaps the shorter fold 12'. The second possibility (shown in FIG. 5) is that the longer fold 12 is wrapped before the shorter fold 12' and thus the longer fold 12 is at least partially overlapped by the shorter fold 12'. These two ways of wrapping give different results that will be discussed herein below.

According to the wrapping configurations of both FIGS. 4 and 5, two cavities 13a, 13b are formed between the folds 12, 12' and the second gap 27: i) a first larger cavity 13a under the internal fold, i.e. the fold 12' or 12, respectively, that has been wrapped first; ii) a second smaller cavity 13b under the external fold, i.e. the fold 12 or 12', respectively, that has been wrapped last.

This allows modulation of the dimensions of the cavities, and thus the amount of drug that can be contained therein. In fact a decrease of the dimension of the first gap 26 between two folds 12, 12' of the same pair allows an increase in the dimension of an adjacent second gap 27 and associated increases in the circumferential width of band 15, the dimensions of the cavities 13a, 13b, and thus the amount of loaded drug 14.

In these embodiments, the two cavities 13a, 13b, especially the internal cavity 13a, are efficiently isolated from the external environment, so that the drug contained therein can hardly be reached by the blood flow and cannot be dispersed in unintended districts of the body before the angioplasty balloon catheter has reached the site of intervention.

In one embodiment of the invention, the longer folds 12 of the angioplasty balloon 1 have substantially the same circumferential length as the second gap 27.

The embodiments shown in FIGS. 3-7 and 18 comprise three pairs of folds 12, 12', 112, but, in other embodiments, the number of pairs may be different depending on the diameter of the balloon, which on its turn will depend on the desired clinical application and the intervention site.

Figure 6:
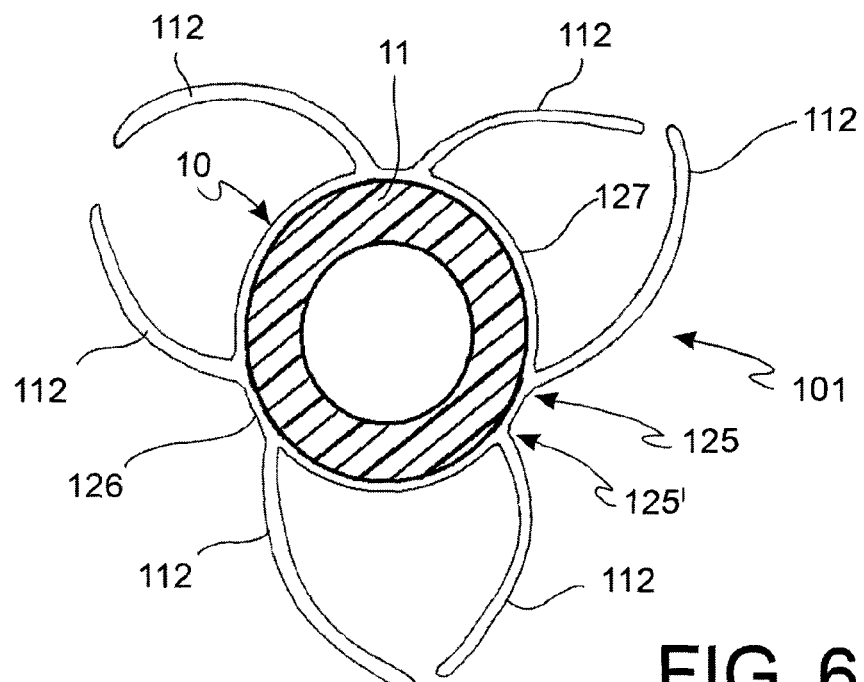
FIG. 6 is a sectional view of another embodiment of the folded balloon catheter of the invention, in an unwrapped collapsed configuration.
Figure 7:
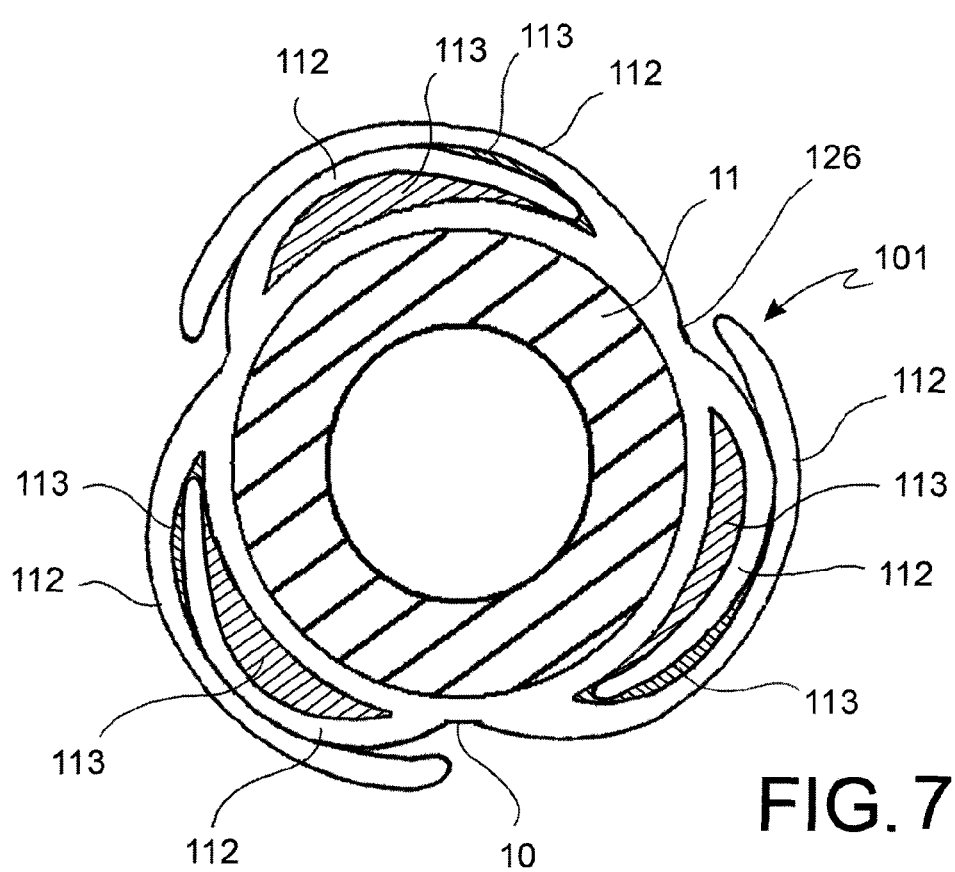
FIG. 7 is a sectional view of the folded balloon catheter of FIG. 6, in a wrapped collapsed configuration.

According to the embodiment shown in FIGS. 6 and 7, the angioplasty balloon 101 comprises three pairs of folds 112, wherein each fold 112 has the same length.

As in this case a plane of symmetry containing the axis X of the balloon is actually present, and the said embodiment will be defined as a "symmetrical configuration" of the collapsed balloon.

The folds 112 of each pair originate from distinct longitudinal lines 125, 125' on the outer surface 10 of the balloon 1 and are separated by a first gap 126.

A second gap 127, having a greater extension than the first gap 126, separates a fold 112 of a pair from a fold 112 of an adjacent pair.

As said above, the first gap 126 has a minor extension which may tend towards zero in order to maximize the second gap 127, for the reason explained above.

As shown in the collapsed configuration of FIG. 7, the folds 112 are circumferentially wrapped around second gaps 127, which are supported by the core 11 in such a way that a fold 112 of one pair is wrapped in one direction—for example in a clockwise direction—and an adjacent fold 112 of an adjacent pair is wrapped in the opposite direction—for example in a counter-clockwise direction—so that the second gap 127 is covered by the wrapped folds. In this embodiment, as the folds 112 have all the same length, it does not matter which fold is wrapped first.

While the folds 112 are wrapped around the second gap 127, a cavity 113 is formed between the lower fold 112 (the fold that has been wrapped first) and band 15 applied along the second gap 127. This cavity 113 provides an efficient tightness and isolation from the external environment, thus preserving the drug 14 contained therein. Furthermore, the single cavity 113 allows that a greater amount of drug 14 can be loaded with respect to the embodiment provided with two distinct cavities 13a and 13b.

In one embodiment of the invention, the folds 112 of the balloon 101 have substantially the same circumferential length as the second gap 127.

Figure 18:
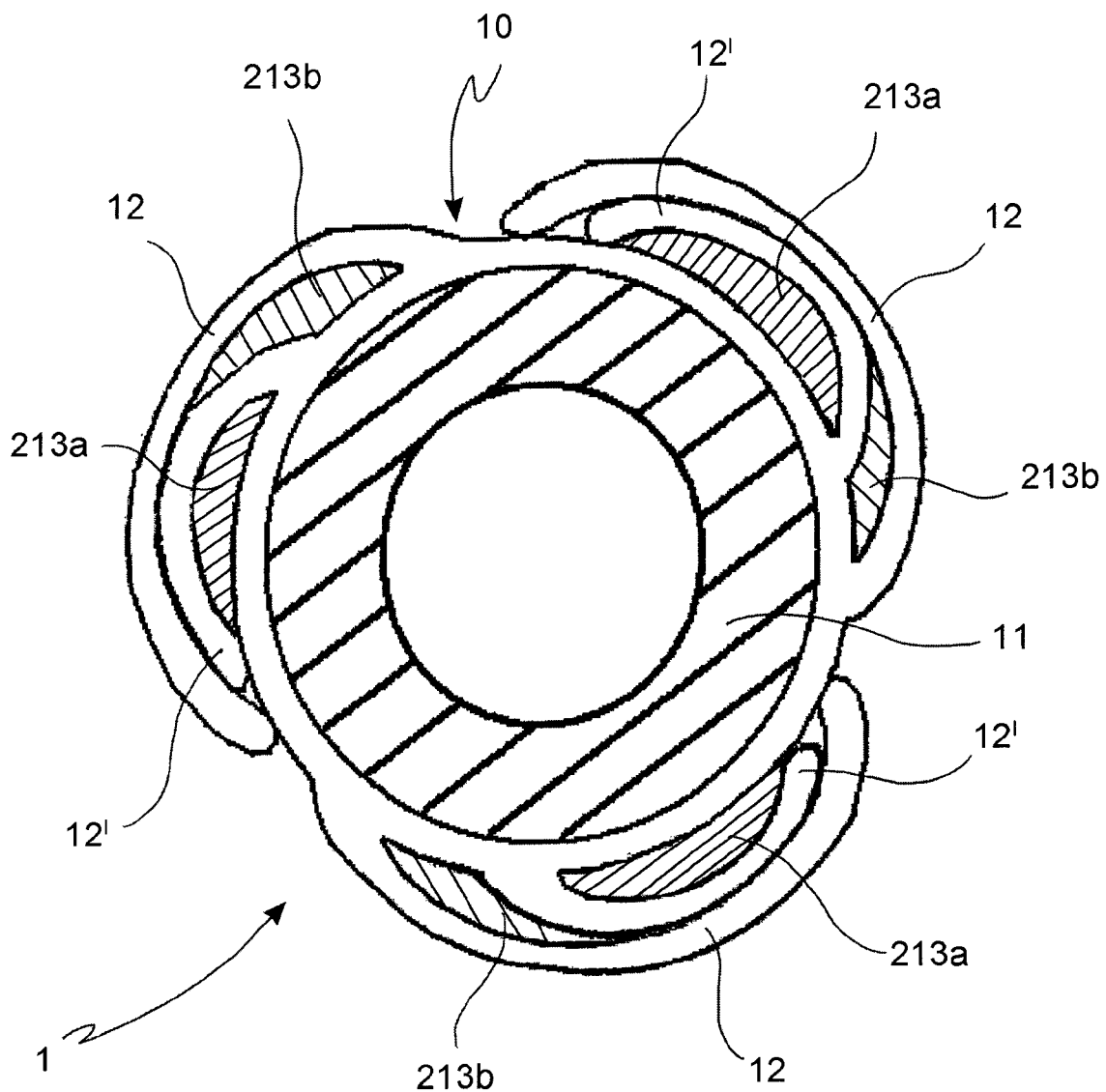
FIG. 18 is a sectional view of the folded balloon catheter of FIG. 3, in a different wrapped configuration.

In accordance with another embodiment of the present invention, as shown in FIG. 18, the folds 12, 12' of the balloon 1 are arranged in pairs and are circumferentially wrapped around the second gap 27 in the same direction.

Preferably, as shown in FIG. 18, a fold 12 and a fold 12' of the same pair are circumferentially wrapped around the second gap 27 in the same direction, so that the two folds of the same pairs overlap.

Alternatively (not shown in the figures) a fold 12 in a pair and the adjacent fold 12' in another pair are circumferentially wrapped in the same direction, i.e. if a fold is wrapped clockwise, also the adjacent fold is wrapped clockwise, so that the two adjacent folds overlap.

According to a further embodiment, three folds 12 of a first length and three folds 12' of a second length are provided when the balloon is in a collapsed configuration, wherein the said first length is greater than the said second length. The folds 12, 12' are circumferentially wrapped in such a way that a shorter fold 12' of one pair is wrapped in one direction and an adjacent longer fold 12 of an adjacent pair is wrapped in the same direction, so that the two adjacent folds overlap.

Preferably, the folds 12, 12' of the same pair are circumferentially wrapped in such a way that a shorter fold 12' is wrapped in one direction and a longer fold 12 of the same pair is wrapped in the same direction, so that the two folds of the same pairs overlap.

Wrapping the folds as described above may be performed in accordance with the following embodiments: the first possibility (shown in FIG. 18) is that the shorter fold 12' is wrapped before the longer fold 12, so that this latter overlaps the shorter fold 12'; the second possibility (not shown in the figures) is that the longer fold 12 is wrapped before the shorter fold 12' and thus the longer fold 12 is at least partially overlapped by the shorter fold 12'.

Preferably, as shown in FIG. 18, the longer fold 12 completely overlaps the shorter fold 12'.

According to the wrapping configuration of FIG. 18, two cavities 213a, 213b are formed between folds 12, 12': i) a first larger cavity 213a under the internal fold, i.e. the fold 12' or 12, respectively, that has been wrapped first; ii) a second smaller cavity 213b under the external fold, i.e. the fold 12 or 12', respectively, that has been wrapped last.

In these embodiments, the two cavities 213a, 213b, especially the internal cavity 213a, are efficiently isolated from the external environment, so that the drug contained therein can hardly be reached by the blood flow and can not be dispersed in healthy districts of the body before the angioplasty balloon catheter has reached the site of intervention.

In these embodiments, the first gap 26 is part of the smaller cavity 213b.

Any drug 14 that is capable of treating or preventing restenosis can be used for the invention purposes. As an example, the drug 14 can be chosen from rapamycin and its analogs, epothilone, everolimus, tacrolimus and pimecrolimus, angiopeptin, lovastatin, topoisomerase inhibitors such as etoposide and topotecan, antiestrogens such as tamoxifen, antimitotics such as vincristine, vinblastine, paclitaxel, docetaxel, antimetabolites such as methotrexate, mercaptopurine, pentostatin, trimetrexate, gemcitabine, azathioprine and fluorouracil, and antibiotics such as doxorubicin hydrochloride, or mixtures thereof.

In preferred embodiments of the invention, the drug 14 is substantially lipophilic.

In accordance with an embodiment of the invention, the drug 14 comprises paclitaxel as the active ingredient. Paclitaxel is available with the trade name of TAXOL®, which is a registered mark of Bristol-Myers Squibb.

The drug 14 can be in any form suitable for the intended application. For example, the drug 14 may be contained in microspheres or in microparticles and/or it can be in crystalline or microcrystalline form.

When paclitaxel is used as the drug 14, it can be in crystalline hydrate form, i.e. di-hydrate form.

In accordance with an embodiment, the drug 14 comprises the active ingredient and a suitable excipient, for example a gel or a paste being suitable to penetrate within the cavities 13a, 13b, 113, 213a, 213b and to adhere to the wall 10 of the balloon 1.

In one embodiment, the drug 14 is applied to the balloon as a solution in a suitable solvent, which is allowed to evaporate after the balloon coating. This solution may contain further excipients.

In one embodiment, a solution of paclitaxel and urea in a solvent is used. In a specific embodiment, the solvent is a mixture of an ether and water, preferably a mixture of tetrahydrofuran and water.

In other embodiments, the drug 14 is contained in or adhered to a polymer coating or a hydrogel coating.

Examples of polymer coatings are described, for instance, in the European patent application published as EP 1 800 702 A1 by Boston Scientific.

Figure 17:
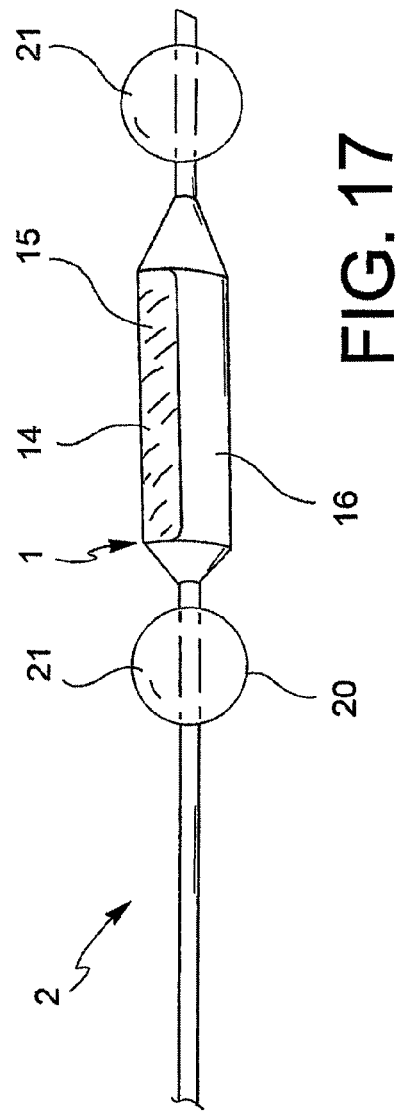
FIG. 17 is a side view of an embodiment of the angioplasty balloon of the invention, in a deployed configuration.

In accordance with further embodiments of the invention, as shown in FIG. 17, the balloon 1 according to the invention comprises containment means 20 that are suitable for stopping the blood flow in the site of intervention.

The containment means 20 allow avoiding the washing effect in the blood flow which tends to remove and disperse the drug 14 immediately after the balloon is inflated and it contacts the vessel walls. In other words, as the blood flow is temporary stopped, the drug is given sufficient time to bind to the vessel walls and to be at least partially absorbed.

In accordance with the embodiment depicted in FIG. 17, the containment means 20 comprise two auxiliary balloons 21, one being located at an immediately proximal position and the other being located at an immediately distal position, relative to the balloon 1.

In accordance with another embodiment (not shown), the containment means 20 comprise an individual auxiliary balloon 21 which is located only at an immediately proximal position relative to the balloon 1.

The auxiliary balloons 21 are suitable to pass from a collapsed configuration, in which they have minimum radial overall dimensions, to a deployed configuration (illustrated in FIG. 17) in which they are suitable to come in contact with the walls of the blood vessel such as to stop the blood flow.

In accordance with an embodiment, the auxiliary balloons 21 are different from the inventive angioplasty balloon 1 in that they comprise an elastic wall which is not suitable to apply a radial force that is typically required for an angioplasty operation. According to this embodiment, the balloon(s) 21 can be made of elastomeric rubber, for instance.

In accordance with an embodiment, the catheter 2 comprises an inflation/deflation duct for the balloon 1 and an individual inflation/deflation duct for the auxiliary balloons 21, even when two of them are provided. In accordance with another embodiment, the catheter 2 comprises an inflation/deflation duct for the balloon 1 and an inflation/deflation duct for each of the auxiliary balloons 21.

In the following description of the procedure for applying the catheter of FIG. 17 in a blood vessel, reference is made to a configuration with two auxiliary balloons 21, but the same operation substantially applies when only one auxiliary balloon 21 is provided. The procedure for using the angioplasty balloon 1, 101 comprises:

inserting the catheter 2 within a blood vessel up to the site of intervention;
  bringing the auxiliary balloons 21 from the collapsed configuration to the deployed configuration;
  bringing the balloon 1, 101 from the collapsed configuration to the deployed configuration such as to carry out the angioplasty operation and the deposition of the drug on the vessel walls;
  bringing the balloon 1, 101 from the deployed configuration to the collapsed configuration;
  after a reasonable time (for example a few seconds), bringing the auxiliary balloons 21 from the deployed configuration to the collapsed configuration;
  removing the catheter.

According to the present invention, a method for obtaining a folded angioplasty balloon 1, 101 which comprises:

forming a plurality of folds 12, 12', 112, wherein the said folds originates from distinct longitudinal lines 25, 25', 125, 125' and are arranged in pairs;
  wrapping the said folds in such a way that a fold of one pair overlaps an adjacent fold of another pair to create cavities 13a, 13b, 113 suitable for receiving a drug 14.

According to an embodiment, the method comprises the step of filling the cavities with said drug 14.

According to a further embodiment, the method comprises the step of applying a plurality of bands 15 of drug 14. Preferably, the step of applying the drug 14 is carried out before the step of forming a plurality of folds 12, 12', 112. Preferably, the bands 15 are axially arranged along the balloon outer wall 10.

It will now be described an apparatus and a method for creating the folds 12, 12', 112 on the angioplasty balloon of the invention.

Figure 10:
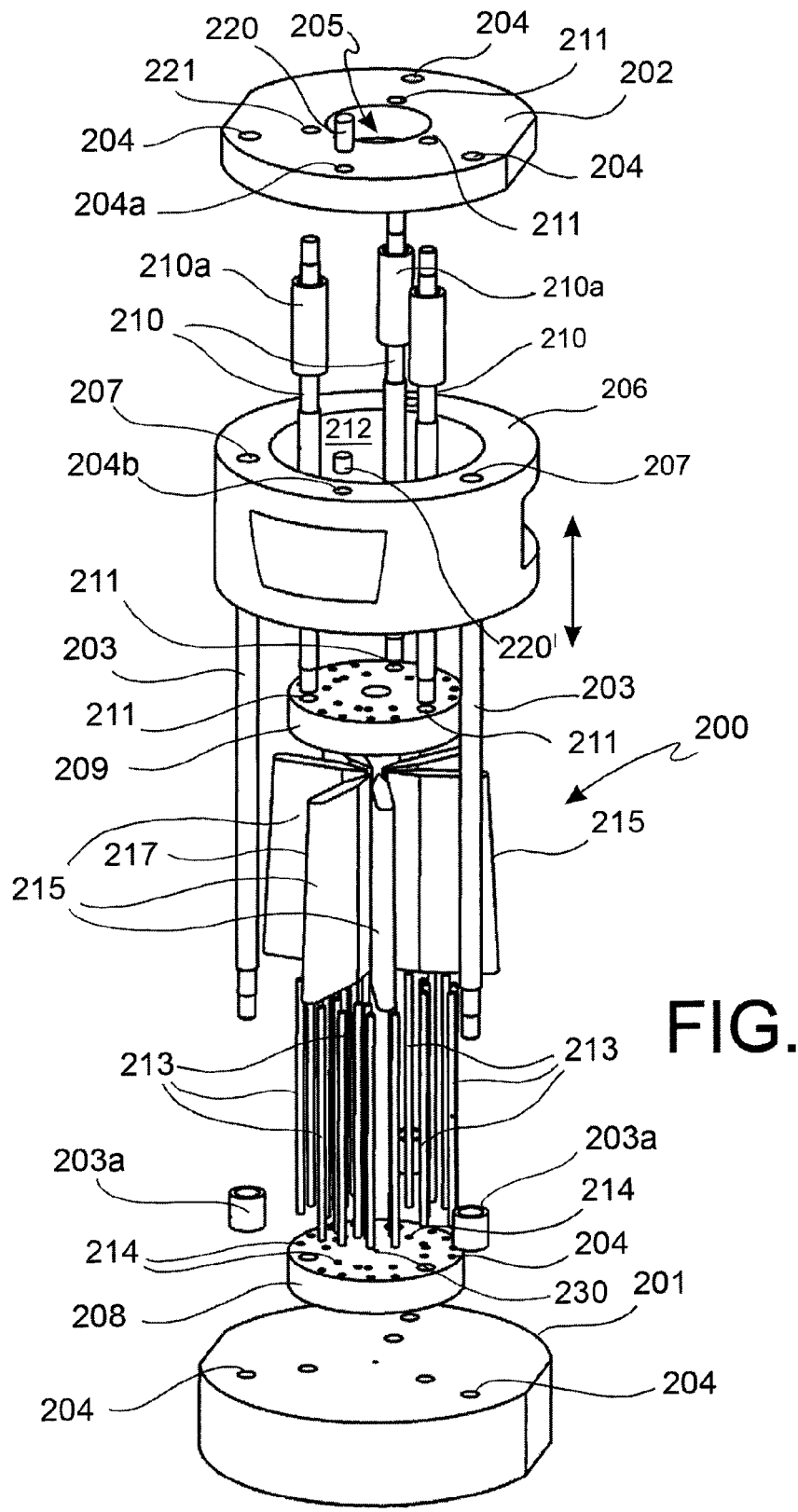
FIG. 10 is an exploded perspective view of an apparatus for the folding of the angioplasty balloon of the invention.

As shown in FIG. 10, an apparatus for creating the folds 12, 12', 112 on an angioplasty balloon 1, 101 is indicated with the numeral 200. The apparatus 200 comprises a base plate 201 and a top plate 202 that are connected by a plurality of columns 203, thus creating an elongated structure having a vertical longitudinal axis. Both the base plate 201 and the top plate 202 comprise holes 204 that are aligned in order to allow the opposite ends of the columns 203 to be inserted therein.

Spacers 203a are provided at the bottom section of the columns 203, to act as stop means.

The top plate 202 comprises a central opening 205 suitable for the insertion of an angioplasty balloon 1, 101.

A cavity 204a in the top plate 202 serves as a seat for a magnet 220.

An actuating means 206 having a central opening 212 is movably arranged between the base plate 201 and the top plate 202. The actuating means 206 comprises through holes 207 aligned with the holes 204 of the base and top plates 201, 202, wherein the columns 203 pass and act as guiding means for the actuating means 206.

A cavity 204b in the top surface of the actuating means 206 serves as a seat for a magnet 220' which, in cooperation with the magnet 220 of the top plate 202, allows hanging the actuating means 206 in a rest position in abutment against the top plate 202.

The central opening 212 of the actuating means 206 has a frustoconical surface which is flaring downwards.

A lower support element 208 is fixed on the base plate 201, while a corresponding upper support element 209 is positioned in a spatial relationship with the top plate 202. A plurality of connecting bars 210, being fixed in corresponding holes 211 in both the upper support element 209 and top plate 202, provide—in cooperation with the spacers 210a associated therewith—for the spaced connection of these two pieces.

The lower support element 208 comprises a central hole 230, which is designed to be a centering means for the angioplasty balloon, as will be described later on.

The width of the upper support element 209 is less than the width of the central opening 212 of the actuating means 206 so that this latter does not interfere with the upper support element 209 when the actuating means is moved up and down.

A plurality of radially movable blades 215 is contained in a sandwich accommodation between the upper and lower support elements 209, 208.

The blades 215 are vertically positioned with their vertical blade edge 216 facing toward the longitudinal axis of the apparatus.

As shown in FIG. 13, the side 217 of the blade 215 opposite to the edge 216 is inclined as the blade width tapers upwards. The inclination of the side 217 of the blade 215 is the same as the inclination of the surface of the opening 212 of the actuating means 206, so that the two surfaces match.

As shown in FIGS. 12A, 12B the blade edge 216 is wedge-shaped and presents a flat tip 216a, 216b whose width is in relation with the geometry of the folds to be formed on the angioplasty balloon.

In particular, according to an embodiment of the invention, a first blade 215a having an edge tip 216a of a first length "l" and a second blade 215b having an edge tip 216b of a second length "L" are provided. An angle γ defines the tapering of the blade thickness to the edge 216, the said angle γ being the same for both blades 215a, 215b. To obtain such two different wedge inclinations and width of the edge tips, the blade sides are beveled. As the width and thickness of the blades 215 are the same, a symmetrical beveling is made to obtain the first blade 215a, while an asymmetrical beveling is made for the second blade 215b, as FIGS. 12A, 12B clearly illustrate. However, it would be possible to provide the first blade 215a of a minor thickness and the second blade 215b of a major thickness, so that in both cases a symmetrical beveling is made.

A first and a second blade 215a, 215b form a pair of blades. According to the embodiment shown in FIGS. 11 and 14, three pairs of blades 215a, 215b are provided, in order to obtain a six-folded balloon. The number of pairs of blades would change if a different type of balloon is desired.

The blades 215a, 215b are arranged with a predefined geometry, which is in relation with the geometry of the folds of the balloon. In particular, an angle α is defined between a first and a second blade 215a, 215b of a pair and an angle β is defined between a first blade 215a of a pair and an adjacent second blade 215b of another pair of blades, wherein β is greater than α. In an embodiment, β is about 80° and α is about 40°.

Figure 14:
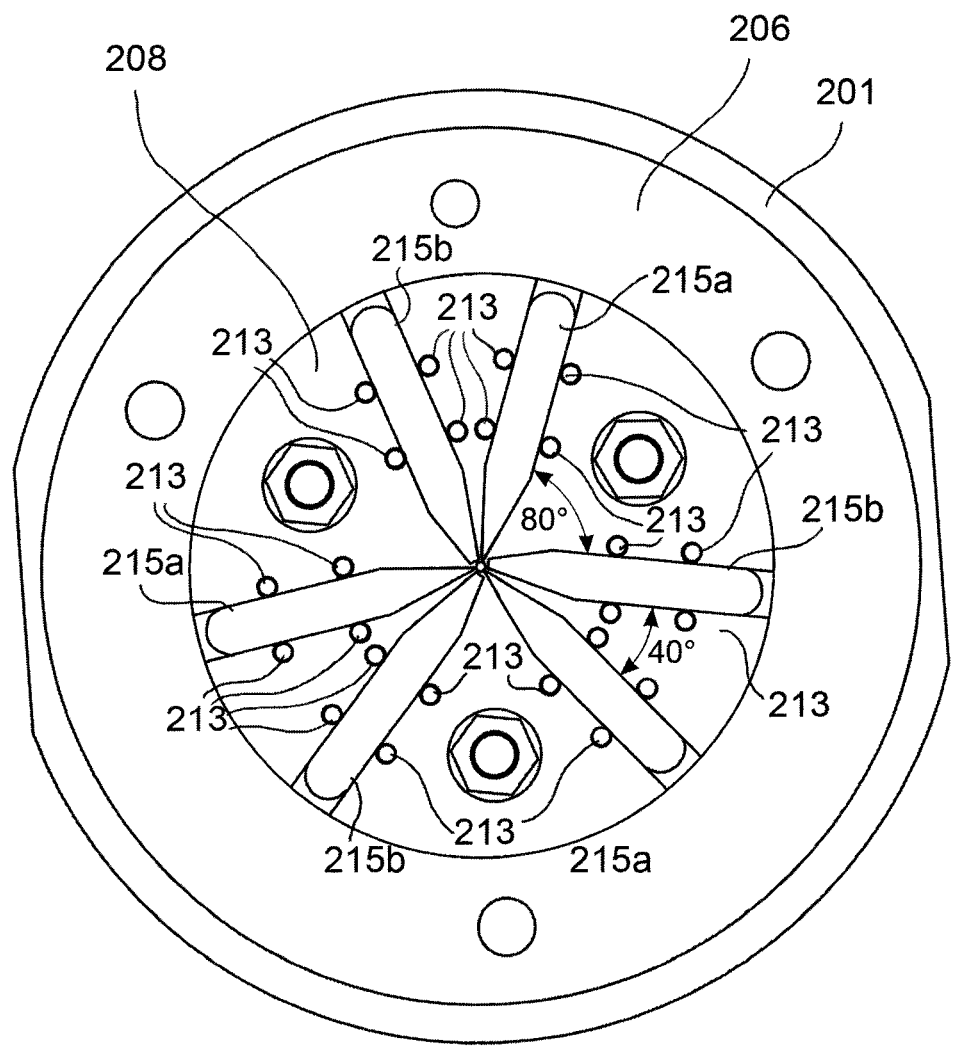
FIG. 14 is a top sectional view of the apparatus of FIG. 10.

As FIG. 14 illustrates, a plurality of connecting pins 213 is inserted in corresponding small holes 214 both in the lower and upper support elements 208, 209 and provides for a double function. First, the connecting pins 213 define a spatial distancing between the two support elements 208, 209. Secondly, the geometrical position of the connecting pins 213 on the support elements matches the predefined geometry of the blades 215a, 215b and forms a race for the blades.

The blades 215a, 215b are made to move in a radial plane, i.e. a plane which contains the longitudinal axis of the apparatus, or in a plane parallel thereto, from a retracted position to an advanced position.

The functioning of the apparatus 200 will now be described.

As said above, the actuating means 206, when in the rest condition, is hanging from the top plate 202, being retained by the magnets 220, 220'. When the actuating means 206 is moved downwards (this can be made manually in the embodiment shown in the drawings, but an automatic actuation can also be provided, such as electrical, pneumatic or the like), it passes around the upper support element 209 and then interacts with the inclined side 217 of the blades 215 (specifically, blades 215a, 215b in the embodiment shown). Such blades 215 are so made to move synchronously from the initial retracted position to an advanced position, towards the longitudinal axis of the apparatus.

When the actuating means 206 is brought back to the resting condition, the blades 215 are free to return to the retracted position. This may be accomplished manually, by means of suitable elastic means (such as a spring) or by any other suitable means.

A procedure for creating the folds 12, 12' on a balloon catheter 1 will be described herein below.

Figure 15A:
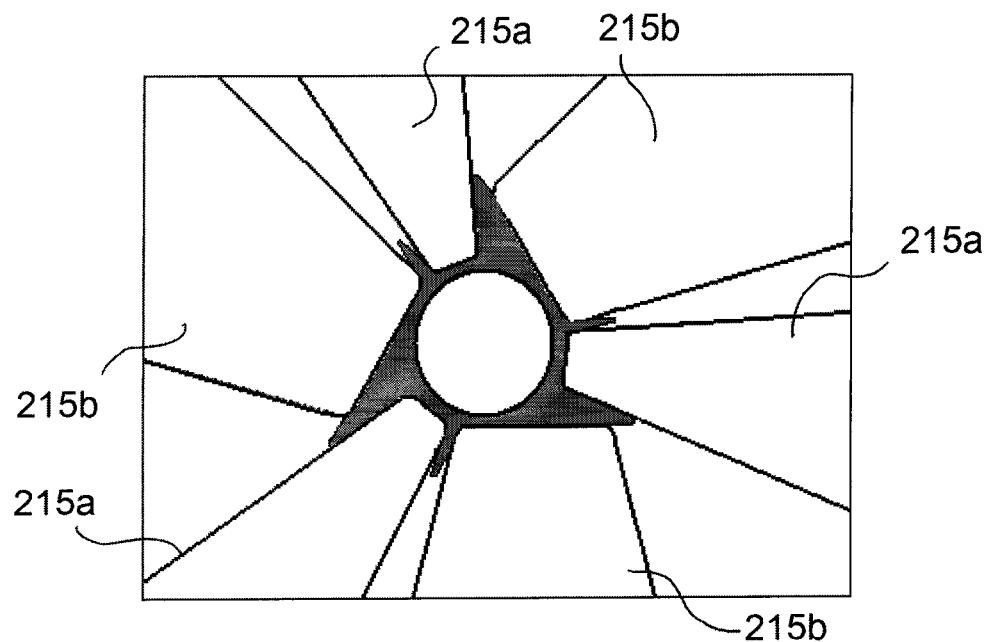
FIG. 15a is a schematic top view showing a first step of the formation of the folds according to the method of the invention.

A balloon catheter is first inserted from the top of the apparatus 200 along the longitudinal axis thereof, until its distal end abuts against the lower support element 208 surface. Then the balloon is inflated or partially inflated. As a next step, the blades 215a, 215b are synchronously actuated by the actuating means 206 and move from their retracted position to their advanced position, where they press and pinch the balloon surface as depicted in FIG. 15A. At this stage, the position and the dimension of the folds 12, 12' are defined. In particular, the extent of the angle α between two blades 215a, 215b of a same pair defines the shorter fold 12', while the extent of the angle β between two adjacent blades of two different pairs defines the longer fold 12.

Figure 15B:
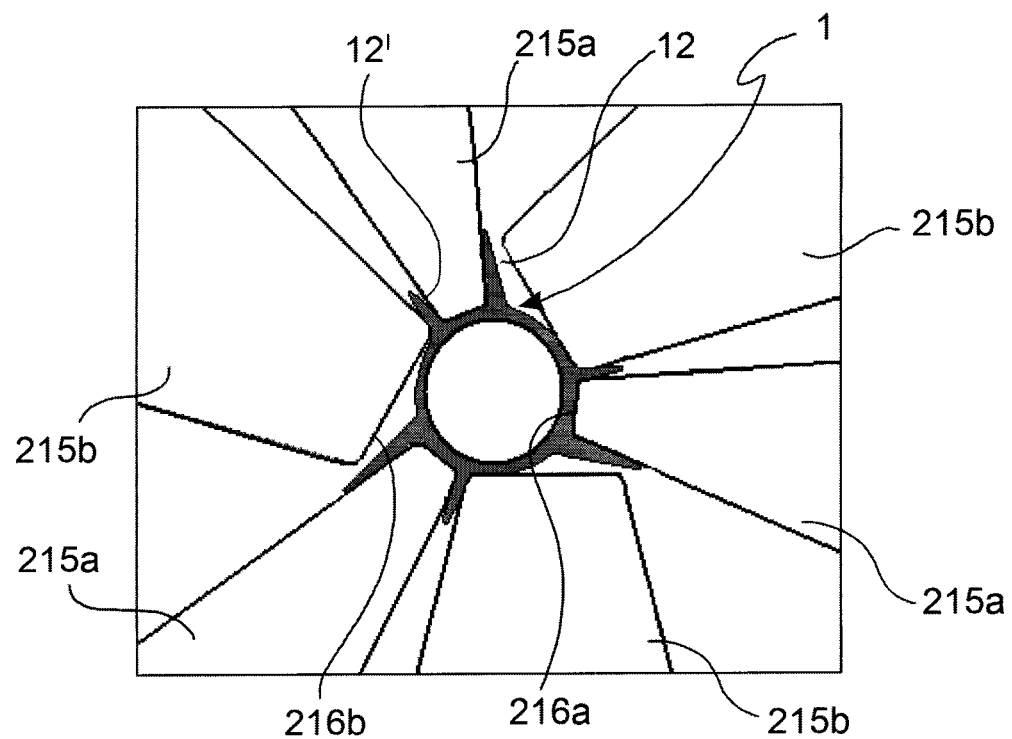
FIG. 15b is a schematic top view showing a second step of the formation of the folds according to the method of the invention.

The balloon is then deflated, so that the folds 12, 12' are finally created (as shown in FIG. 15B).

The folds are then wrapped as explained above, by wrapping first a shorter fold 12' of one pair in one direction—for example, in a clockwise direction—and then an adjacent longer fold 12 of an adjacent pair in the opposite direction—for example, in a counter-clockwise direction—so that the second gap 27 results to be covered by the wrapped folds. As described before, it is possible to wrap first the longer fold 12 and then the shorter fold 12', to arrive to the configuration shown in FIG. 5. As described before, it is possible to wrap the longer fold 12 and the shorter fold 12' in the same circumferential direction, to arrive to the configuration shown in FIG. 18.

If a symmetrical folded balloon is desired, as illustrated in FIGS. 6 and 7, or if the width of the first and second gaps 26, 27 or 126, 127 should be varied, the widths "l" and "L" of the edge tip 216a, 216b of the blades 215a, 215b, as well as the angles α and β between the blades will be suitably adapted.

It is therefore provided a method for obtaining a folded angioplasty balloon 1, 101, which comprises:
  a) inserting the said angioplasty balloon along the longitudinal axis of the above described apparatus 200;
  b) wholly or partially inflating the said angioplasty balloon, wherein steps a) and b) are performed in any order;
  c) synchronously moving the blades 215, 215a, 215b from a retracted position to an advanced position wherein the edge tip 216a, 216b of the blades presses the surface of the angioplasty balloon;
  d) deflating the angioplasty balloon in order to obtain a collapsed folded balloon wherein a plurality of folds 12, 12', 112 and first and second gaps 26, 27, 126, 127 between the folds are created;
  e) wrapping a fold 12, 12', 112 of one pair in one direction and then an adjacent fold 12, 12', 112 of an adjacent pair in the opposite direction, so that the second gaps 27, 127 result to be covered by the wrapped folds and the folds 12, 12', 112 substantially overlap;
  f) repeating step e) for each pair of folds 12, 12',112, so that a wrapped folded angioplasty balloon 1, 101 is obtained, wherein cavities 13a, 13b, 113 are created under the folds, the said cavities being apt to be loaded with a drug 14.

In order to arrive to the configuration shown in FIG. 18, the method for obtaining a folded angioplasty balloon 1 comprises the steps from a to d, as indicated above, and comprises also:
  e') wrapping a fold 12, 12' of a pair in one direction and then the other fold 12', 12 of the same pair in the same direction,
  f') repeating step e') for each pair of folds 12, 12', so that a wrapped folded angioplasty balloon 1, is obtained, wherein cavities 213a, 213b, are created under the folds, the said cavities being apt to be loaded with a drug 14.

Step a) above comprises:
  inserting a stylet into the central hole of the angioplasty balloon catheter of the invention;
  inserting the angioplasty balloon along the longitudinal axis of the apparatus 200 until the stylet tip abuts into the central hole 230 of the lower support element 208 of said apparatus 200.

To manufacture a drug eluting folded angioplasty balloon 1, 101 according to the invention, the above depicted method further includes a step g) of loading the said cavities 13a, 13b, 113, 213a, 213b with a drug 14.

The drug 14 can be loaded in the cavities of the folded balloon of the invention in any suitable way apt to allow the drug or a drug composition to be deposited under the preformed folds.

According to an embodiment, a syringe filled with a solution of the drug 14 is inserted in the cavities 13a, 13b, 113, 213a, 213b from one of the openings 150 (see FIG. 8) formed at the two longitudinal ends of the balloon while wrapping the folds. The syringe must have a needle sufficiently long to arrive to the opposed end of the cavity to be loaded. The delivery of the drug solution is started while retracting the needle, so that the cavity is filled along its whole length.

Preferably, a small portion of the cavity close to both ends is left free of drug, to avoid that, during the clinical use of the balloon, the blood stream could take the drug from these more external recesses.

According to this embodiment, only the cavities 13a, 13b, 113, 213a, 213b under the folds are loaded with the drug 14, while the external surface exposed to the blood stream is free of drug.

Another embodiment of the invention provides for dipping the balloon 1 into a solution of the drug 14 or depositing in any other way the drug onto the balloon surface, when the balloon is still in the deployed condition, then performing the steps a) to f) according to the folding method depicted above. In this way, the drug 14 is loaded both under the folds and on the external surface thereof.

In a preferred embodiment, a further step of removing the drug from the surface outside the folds is performed. The removal of the drug may be done by a dry treatment, i.e. a mechanical removal (for example with a suitable blade or brush), or by a washing treatment with a suitable solvent or by a combination of such methods. In this case, the removed drug can be recovered for a further reuse.

Figure 16:
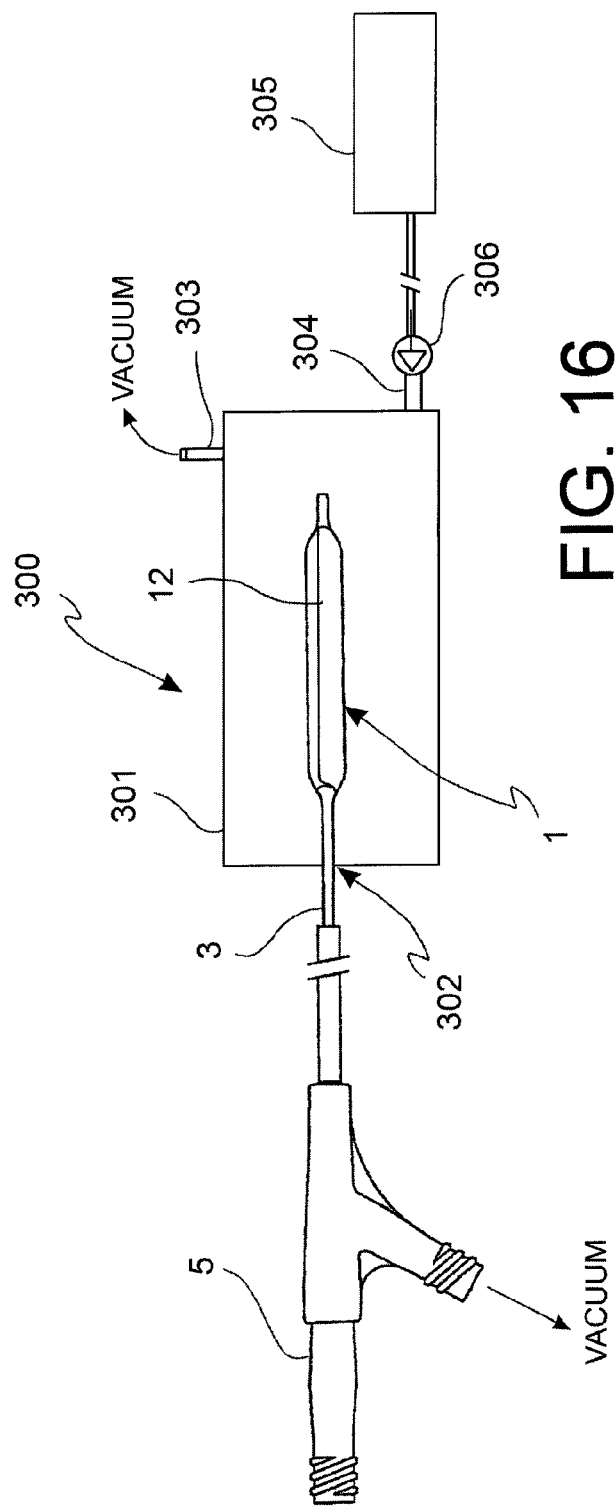
FIG. 16 is a schematic side view of a device for the loading of a drug on an angioplasty balloon of the invention, in a folded collapsed configuration.

According to a further embodiment of the present invention, a device 300 for loading the drug 14 onto the angioplasty balloon 1, 101 is provided (see FIG. 16).

The device 300 comprises a chamber 301 apt to accommodate the distal end of a balloon catheter carrying the angioplasty balloon 1, 101 of the invention. The chamber 301 is tightly closed and comprises a sealed aperture 302 through which the catheter 3 passes, an outlet 303 connected to a vacuum source and an inlet 304 connected to a reservoir 305 containing a suitable solution of the drug 14. Between the reservoir 305 and the inlet 304 valve means 306 are provided to start or stop the delivery of the drug solution into the chamber 301. The lumen 4, 4' of the catheter 2 for the inflation/deflation of the angioplasty balloon is also connected, through the connector means 5, with a vacuum source.

The folded and wrapped balloon 1, 101 is accommodated in the chamber 301 with a catheter 2 section passing through the aperture 302, then the chamber is tightly closed. As the catheter 2 tip is normally open, a closure (not shown) should be provided thereon, to avoid that the chamber 301 is put into communication with the exterior.

Vacuum is made into the chamber 301 through the outlet 303, so that all the air under the folds 12, 12', 112 is extracted and the folds are slightly opened. Then the vacuum source is closed and the valve means 306 are open, allowing the drug solution to fill in the chamber 301. The drug loads both the cavities 13a, 13b, 113, 213a, 213b under the folds and the external surface of the balloon. Vacuum is then applied into the balloon through the connector means 5, so that the folds are tightly wrapped again around the core 11. Finally, the chamber 301 is emptied and the balloon is extracted.

In a preferred embodiment, a further step of removing the drug from the surface outside the folds is performed. The removal of the drug may be done by a dry treatment, i.e. a mechanical removal (for example with a suitable blade or brush), or by a washing treatment with a suitable solvent or by a combination of such methods.

In accordance with further embodiments, at the end of the step of loading the cavities 13a, 13b, 113, 213a, 213b with the drug 14, the balloon 1, 101 is protected with a protective sheath. The protective sheath has the purpose of keeping the folds in position, such that the drug 14 does not escape from the cavities.

Alternatively, the protective sheath is positioned on the balloon during the step of loading the cavities 13a, 13b, 113, 213a, 213b with the drug 14.

From what has been set forth above, those skilled in the art may appreciate that the balloon according to the invention can at least partially overcome the drawbacks of prior art balloons.

In fact, the balloon according to the invention, when in the collapsed configuration, protects the drug 14 by means of the folds 12, 12', 112. In other words, when the balloon 1 is in the collapsed configuration, the drug 14 is not exposed to contact with the external environment and only the strips 16 of the wall not covered with drug 14 are exposed. This characteristic allows the balloon to be advanced along the vessels of the circulatory system without dispersing the drug in healthy districts along the pathway.

Although preferred embodiments of the invention have been described in detail, it is not the intention of the applicant to limit the scope of the claims to such particular embodiment, but to cover all modifications and alternative constructions falling within the scope of the invention.

The invention claimed is:

1. A drug eluting angioplasty balloon suitable to adopt a deployed configuration and a collapsed configuration, the balloon having an outer wall disposed around a core defining an axis, the balloon comprising in the collapsed configuration a plurality of folds that are laid in a tangential direction about the core of the balloon and form a plurality of cavities loaded with a drug, the said cavities are comprised between the said folds, wherein:
the folds originates from distinct longitudinal lines along the outer wall and are arranged in pairs;
the folds are circumferentially wrapped about the core in such a way that a fold of one pair overlaps an adjacent fold of another pair, and
a fold of one pair and the adjacent fold of another pair are wrapped in opposite directions, wherein the folds in one pair are separated by a first gap and a fold of a pair is separated from an adjacent fold of another pair by a second gap, wherein said second gap is greater than said first gap and wherein said cavities are formed between said substantially overlapping folds and said second gaps.

2. The angioplasty balloon of claim 1, wherein the folds are single-folded.

3. The angioplasty balloon according to claim 1, wherein a fold of one pair substantially overlaps an adjacent fold of another pair.

4. The angioplasty balloon according to claim 3, wherein a fold of one pair overlaps for at least 60% of its circumferential length the adjacent fold of another pair.

5. The angioplasty balloon according to any claim 1, wherein folds of a first length and folds of a second length are provided, wherein the first length is greater than the second length to define shorter folds and longer folds, a longer fold and a shorter fold forming the pair of folds.

6. The angioplasty balloon according to claim 5, wherein a longer fold of one pair of folds overlaps an adjacent shorter fold of another pair of folds, so that two cavities are defined between the longer and shorter folds and the gap.

7. The angioplasty balloon according to claim 5, wherein a shorter fold of one pair of folds overlaps an adjacent longer fold of another pair of folds, so that two cavities are defined between the longer and shorter folds and the gap.

8. The angioplasty balloon according to claim 1, wherein the folds have all the same length.

9. The angioplasty balloon according to claim 8, wherein the said folds have substantially the same extension as the second gaps.

10. The angioplasty balloon according to claim 1, being mounted on a catheter further comprising containment means for stopping the blood flow.

11. The angioplasty balloon according to claim 10 wherein the containment means comprise an auxiliary balloon that is placed in an immediately proximal position relative to the balloon, the auxiliary balloon, when in the deployed configuration, being suitable to come in contact with the walls of a blood vessel such as to stop the blood flow.

12. The angioplasty balloon according to claim 10, wherein the containment means comprise two auxiliary balloons that are placed in immediately proximal and immediately distal positions relative to the balloon, the said auxiliary balloons, when in the deployed configuration, being suitable to come in contact with the walls of a blood vessel such as to stop the blood flow.

13. A drug eluting angioplasty balloon suitable to adopt a deployed configuration and a collapsed configuration, having an outer wall disposed around a core defining an axis, the balloon comprising in the collapsed configuration a plurality of folds that are laid in a tangential direction about the core of the balloon and form a plurality of cavities loaded with a drug, wherein:
the folds originates from distinct longitudinal lines along the outer wall and are arranged in pairs, and
folds of a first length and folds of a second length are provided, wherein the first length is greater than the second length to define shorter folds and longer folds, a longer fold and a shorter fold forming the pair of folds.

14. The angioplasty balloon of claim 13, wherein a longer fold of one pair of folds overlaps an adjacent shorter fold of another pair of folds, so that two cavities are defined between the longer and shorter folds and the said core.

15. The angioplasty balloon according to claim 13, wherein a shorter fold of one pair of folds overlaps an adjacent longer fold of another pair of folds, so that two cavities are defined between the longer and shorter folds and the core.

16. The angioplasty balloon according to claim 13, wherein a shorter fold of one pair and an adjacent longer fold of an adjacent pair are wrapped in the same direction, so that the two adjacent folds overlap.

17. The angioplasty balloon according to claim 13, wherein a shorter fold of one pair and a longer fold of the same pair are wrapped in the same direction, so that the two folds overlap.

18. The angioplasty balloon according to claim 17, wherein the shorter fold is wrapped before the longer fold so that this latter overlaps the shorter fold.

19. The angioplasty balloon according to claim 18, wherein the longer fold completely overlaps the shorter fold.

* * * * *

UNITED STATES PATENT AND TRADEMARK OFFICE
CERTIFICATE OF CORRECTION

| | | |
|---|---|---|
| PATENT NO. | : 9,168,362 B2 | Page 1 of 1 |
| APPLICATION NO. | : 13/885377 | |
| DATED | : October 27, 2015 | |
| INVENTOR(S) | : Morero et al. | |

It is certified that error appears in the above-identified patent and that said Letters Patent is hereby corrected as shown below:

In the Claims

In column 15, line 29 "...the said cavities are comprised..." should read -- ...the cavities are comprised... --

In column 15, line 52 "...according to any claim 1..." should read -- ...according to claim 1... --

In column 16, line 8 "...the said folds have substantially..." should read -- ...the folds have substantially... --

In column 16, line 22 "...the said auxiliary..." should read -- ...the auxiliary... --

In column 16, line 42 "...folds and the said core." should read -- ...folds and the core. --

Signed and Sealed this
Tenth Day of May, 2016

Michelle K. Lee
*Director of the United States Patent and Trademark Office*